United States Patent [19]

Lindsay et al.

[11] Patent Number: 4,863,441
[45] Date of Patent: Sep. 5, 1989

[54] VENOUS RETURN CATHETER

[75] Inventors: Erin J. Lindsay, Manchester; James B. Howell, Ann Arbor, both of Minn.

[73] Assignee: Minnesota Mining and Manufacturing Company, St. Paul, Minn.

[21] Appl. No.: 150,340

[22] Filed: Jan. 27, 1988

Related U.S. Application Data

[63] Continuation-in-part of Ser. No. 74,695, Jul. 17, 1987, abandoned.

[51] Int. Cl.$^4$ ............................................. A61M 25/00
[52] U.S. Cl. ..................................... 604/280; 604/264
[58] Field of Search .............................. 604/280–283, 604/264, 269, 43, 93, 4, 284, 44, 45, 274; 128/656, 658

[56] References Cited

U.S. PATENT DOCUMENTS

| 3,630,207 | 12/1971 | Kahn et al. | 604/282 |
|---|---|---|---|
| 4,129,129 | 12/1978 | Amrine | 128/214 R |
| 4,596,548 | 6/1986 | DeVries et al. | 604/4 |
| 4,639,252 | 1/1987 | Kelly et al. | 604/282 |
| 4,680,029 | 7/1987 | Ranford et al. | 604/280 |
| 4,717,379 | 1/1988 | Ekholmer | 604/280 |
| 4,784,638 | 11/1988 | Ghajar et al. | 604/280 |

*Primary Examiner*—Dalton L. Truluck
*Assistant Examiner*—Denise Whelton
*Attorney, Agent, or Firm*—Donald M. Sell; Walter N. Kirn; Robert W. Hoke, II

[57] ABSTRACT

A kink-resistant, dual-drainage, venous return catheter preferably completely comprised of a polyvinyl chloride material and molded in a conventional injection molding process. This catheter comprises a smaller portion dimensioned to be received in a vena cava, a larger portion and a transition portion between the two other portions. In one embodiment, the transition portion comprises means for stinting the larger portion so that it can't enter the vena cava, a plurality of inlet openings and a plurality of reinforcing channels connecting the inlet openings to the larger portion so that fluid entering the inlet openings is channeled into the larger portion. All of these openings are preferably peripherally chamfered on the inside generally away from the smaller catheter portion and on the outside generally towards and away from the smaller catheter portion.

18 Claims, 3 Drawing Sheets

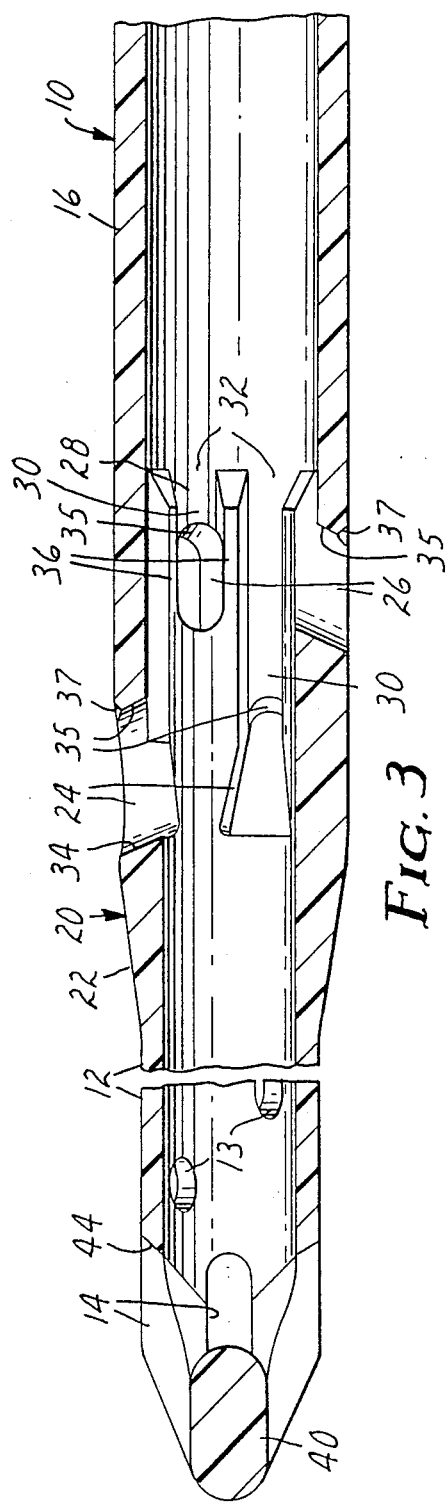
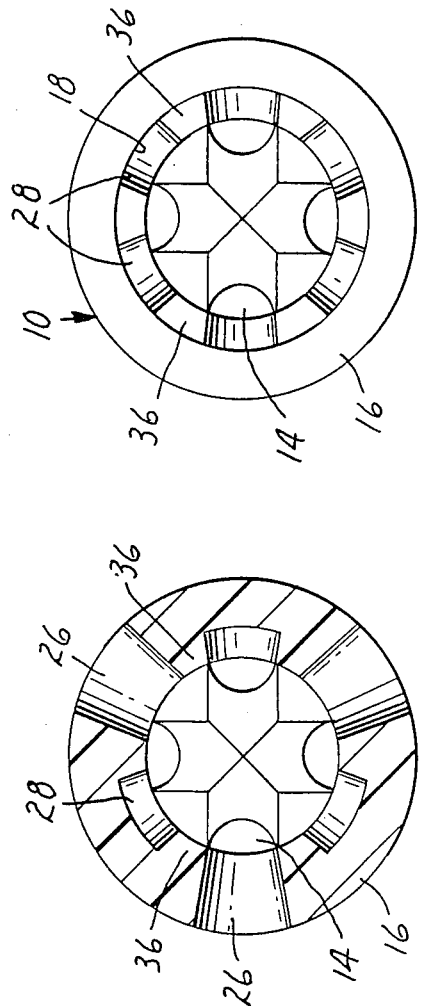
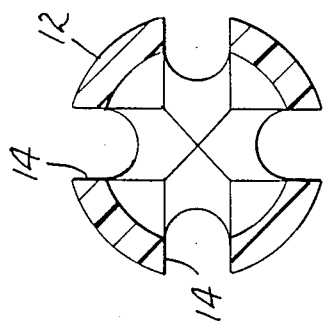
FIG. 3
FIG. 4
FIG. 5
FIG. 6

4,863,441

VENOUS RETURN CATHETER

Cross-Reference to Related Application

This application is a continuation-in-part of U.S. patent application Ser. No. 074,695, filed July 17, 1987 now abandoned.

FIELD OF THE INVENTION

This invention relates to medical catheters and in one aspect to a medical catheter suitable for draining fluid from a vena cava and from a right atrium of a human heart into extracorporeal life support equipment.

BACKGROUND ART

Extracorporeal life support equipment is used during extracorporeal cardiopulmonary bypass to mechanically perform the functions normally performed by the heart and lungs. The venous blood, which is depleted in oxygen and rich in carbon dioxide, is mechanically removed from the patient via medical catheters and connecting tubing and pumped to oxygenating apparatus. The oxygenated blood is later returned to the patient's arterial system via further medical tubes and medical catheters.

The medical catheters used to drain the venous blood are generally known as venous return catheters. U.S. Pat. Nos. 4,639,252 and 4,129,129 describe such catheters to be of a single or of a dual drainage construction. The dual drainage construction includes drainage openings at the distal end and also along the catheter's length proximal to the distal end. This is known to many times eliminate the need for a second catheter requiring a second entry incision or wound in the wall of the heart. Dual-drainage catheters are typically inserted through the right atrium and into the inferior vena cava with the proximal drainage openings positioned within the right atrium. This placement permits blood to be drained simultaneously from the vena cava in which the dual-drainage catheter is placed and from the right atrium.

As noted in the foregoing patents, it is exceedingly important that adequate volumes of blood be drained from the patient during cardiopulmonary bypass so that the extracorporeal life support equipment can keep up with the patient's need for oxygen and can adequately remove excess carbon dioxide. Insufficient quantities of oxygen can lead to serious tissue damage.

As pointed out in U.S. Pat. No. 4,639,252, some surgical procedures require manipulation or movement of the heart. Since the inferior vena cava is substantially anchored in place, manipulation of the heart frequently increases the angle of bend in the portion of the catheter situated at the juncture between the inferior vena cava and the right atrium. Not uncommonly, according to this patent, the increased degree of bending causes the catheter to become kinked. This is said to restrict or even interrupt blood drainage from the inferior vena cava.

The dual-drainage catheter described in U.S. Pat. No. 4,639,252 is reinforced in the area of the proximal drainage openings to minimize such kinking. This reinforcement is described as a reinforcing member 24 in the form of a layer of 90 Shore A durometer polyvinyl chloride material having a thickness of about 1 millimeter with the proximal drainage openings being punched through this layer.

SUMMARY OF THE INVENTION

The present invention provides a kink-resistant, dual-drainage, venous return catheter without the need for a separate layer of reinforcement. This simplified catheter construction can permit an adequate venous blood flow with a relatively smaller cross-sectional flow area. This, in turn, permits a smaller wound to be made in the heart.

This medical catheter is preferably injection molded from a plastic material and comprises a first cross-sectional area catheter portion having at least one inlet opening, a second, larger cross-sectional area catheter portion having an outlet opening and a transition catheter portion between the first and second catheter portions and in fluid communication with the first and second catheter portions. The first cross-sectional area catheter portion is dimensioned to be received within a vena cava.

In one embodiment, the transition catheter portion comprises (1) means adjacent the first cross-sectional area catheter portion for stinting the second, larger cross-sectional area catheter portion so that the second catheter portion cannot enter the vena cava, (2) a plurality of inlet openings adjacent the stinting means and (3) a plurality of generally longitudinally-aligned, reinforcing channels disposed along the inside of the transition catheter portion. These channels each have one end connected to the inlet openings, and their other ends connected to the second, larger cross-sectional area catheter portion. Fluid entering the inlet openings of the transition catheter portion is channeled into the second, larger cross-sectional area catheter portion together with fluid entering the inlet opening of the first cross-sectional area catheter portion.

In a preferred embodiment, the first cross-sectional area catheter portion generally comprises a cylinder, and the stinting means generally comprises a diameter-increasing protrusion. Also in the preferred embodiment, the inlet openings of the transition catheter portion comprise a plurality of generally triangularly-shaped openings disposed about the transition catheter portion adjacent the diameter-increasing protrusion and a plurality of generally elongated openings disposed about the transition catheter portion adjacent the triangularly-shaped openings. All of these openings are preferably peripherally chamfered on the inside, generally away from the first cross-sectional area catheter portion and on the outside generally towards and away from the first cross-sectional area catheter portion.

BRIEF DESCRIPTION OF THE DRAWING

The invention is illustrated in the accompanying drawing wherein like numbers refer to like parts.

FIG. 3 is an enlarged, sectional view of the medical catheter of FIG. 1 taken approximately along the line 3—3 of FIG. 2 with portions broken away.

FIG. 4 is an enlarged, end view of the proximal end of the medical catheter of FIG. 1.

FIG. 5 is an enlarged, cross-sectional view of the medical catheter of FIG. 1 taken approximately along the line 5—5 of FIG. 2.

FIG. 6 is an enlarged, cross-sectional view of the medical catheter of FIG. 1 taken approximately along the line 6—6 of FIG. 2.

DETAILED DESCRIPTION

Figure 1:
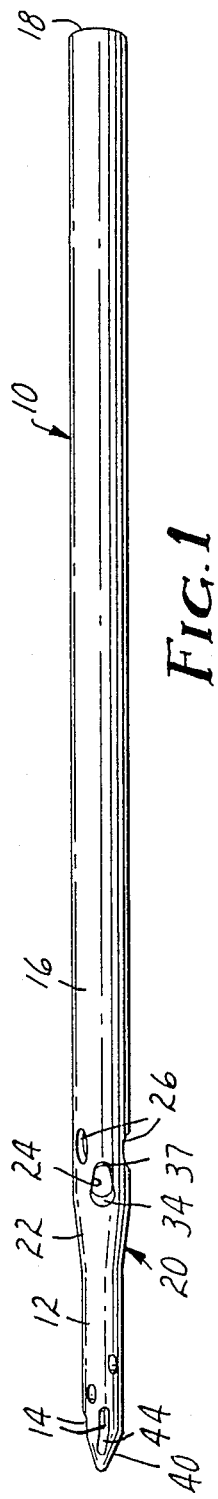
FIG. 1 is a perspective view of a preferred embodiment of the medical catheter of the present invention.

Referring to the figures of the drawing, there is shown in FIG. 1 a perspective view of a preferred embodiment of the medical catheter 10 of the present invention. The medical catheter 10 is generally comprised of a first cross-sectional area catheter portion 12 having an inlet opening or openings 13 and 14 through a cone-shaped distal end portion 40, a second, larger cross-sectional area catheter portion 16 having an outlet opening 18 and a transition catheter portion 20 between the first and second catheter portions 12 and 16. The transition catheter portion 20 is in fluid communication with the first and second catheter portions 12 and 16.

The first cross-sectional area catheter portion 12 is preferably dimensioned to be received within a vena cava, preferably the inferior vena cava, not shown. The second, larger cross-sectional area catheter portion is preferably dimensioned not to be received within the vena cava; that is, this second catheter portion is preferably too large to be received within the vena cava.

As perhaps best shown in FIG. 3, the transition catheter portion 20 is generally comprised of a means 22 adjacent the first cross-sectional area catheter portion 12 for stinting the second, larger cross-sectional area catheter portion 16 so that the second catheter portion 16 cannot enter the vena cava even if appropriately dimensioned, a plurality of inlet openings 24 and 26 adjacent the stinting means 22 and a plurality of generally longitudinally-aligned, reinforcing channels 28 disposed along the inside of the transition catheter portion 20 as shown in FIGS. 3, 4 and 5. The first cross-sectional area catheter portion 12 preferably generally comprises a cylinder, and the stinting means 22 generally comprises a diameter-increasing protrusion.

The reinforcing channels 28 each have one end 30 connected to the inlet openings 24 and 26 of the transition catheter portion 20 and the other ends 32 are connected to the second, larger cross-sectional area catheter portion 16. Fluid entering the inlet openings 24 and 26 is channeled into the second, larger cross-sectional area catheter portion 16 by the channels 28 together with fluid entering the inlet opening 14 of the first cross-sectional area catheter portion 12 with a minimum of interference between these fluid flows, thereby reducing fluid pressure drop across the medical catheter 10.

In the preferred embodiment, the inlet openings 24 and 26 comprise a plurality of generally triangularly-shaped openings 24 disposed about the transition catheter portion 20 adjacent the diameter-increasing protrusion 22 with one side of each triangle generally transverse to the length of the medical catheter 10 and a plurality of generally elongated openings 26 disposed about the transition catheter portion 20 adjacent the triangularly-spaced openings 24. As shown in FIG. 3, these openings 24 and 26 are preferably peripherally chamfered on the outside and on the inside. Most preferably, openings 24 and 26 are peripherally chamfered on the outside generally towards and away from the first cross-sectional area catheter portion 12 with longitudinally-aligned chamfers 34 and 37 and on the inside generally away from the first cross-sectional area catheter portion 12 with longitudinally-aligned chamfers 35.

The chamfers 35 are preferably between 30° and 70° with respect to the length of the medical catheter 10 and most preferably are about 45°. The chamfers 34 and 37 reduce tissue trauma upon catheter insertion and withdrawal from the wound in the heart and reduce fluid pressure drop across the medical catheter 10. These chamfers 34 and 37 together with the chamfers 35 and the channels 28 significantly reduce the pressure drop across the medical catheter 10 as compared to an otherwise substantially identical medical catheter 10 without these chamfers 34, 35 and 37 and channels 28. This reduced pressure drop translates into a higher fluid flow rate for a given medical catheter 10 or can be capitalized upon to downsize the catheter 10. The later has the advantage of providing an adequate venous blood flow with a relatively smaller cross-sectional flow area which, in turn, permits a smaller wound to be made in the heart.

The channels 28 facilitate the fluid flow from the openings 24 and 26 to the second, larger cross-sectional area catheter portion 16 and also reinforce the transition catheter portion 20 in the area of the openings 24 and 26 to resist kinking of the medical catheter 10 in this area in the event that the catheter 10 is bent in use. As noted earlier, U.S. Pat. No. 4,639,252 describes some surgical procedures as including bending dual-drainage catheters when manipulating or moving the heart.

The channels 28 are comprised of a plurality of longitudinally-aligned, reinforcing rails 36 with each rail 36 forming a common wall between a channel 28 connected to a triangularly-shaped opening 24 and a channel 28 connected to an elongated opening 26. In this configuration, as perhaps best shown in FIG. 5, the openings 24 and 26 are generally equidistantly disposed about the circumference of the transition catheter portion 20 in an alternating fashion with one triangularly-shaped opening 24 and connected channel 28 generally between two elongated openings 26 and connected channels 28, and vice versa.

Figure 7:
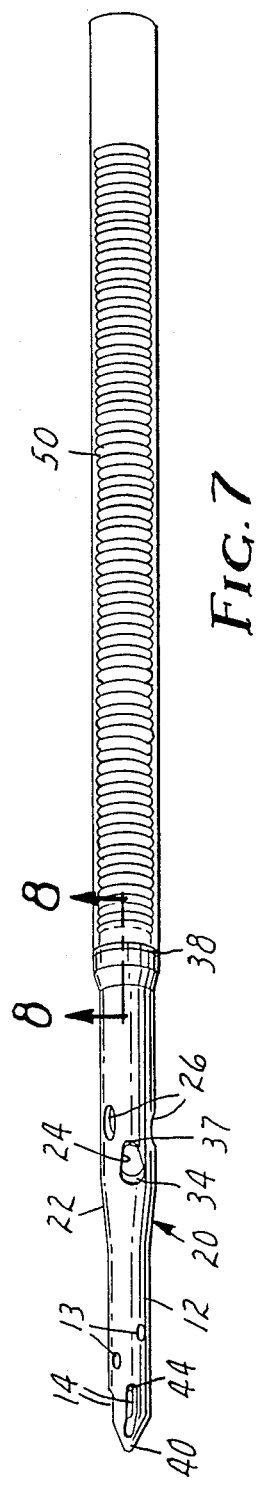
FIG. 7 is a perspective view of an alternate embodiment of the medical catheter of the present invention.
Figure 8:
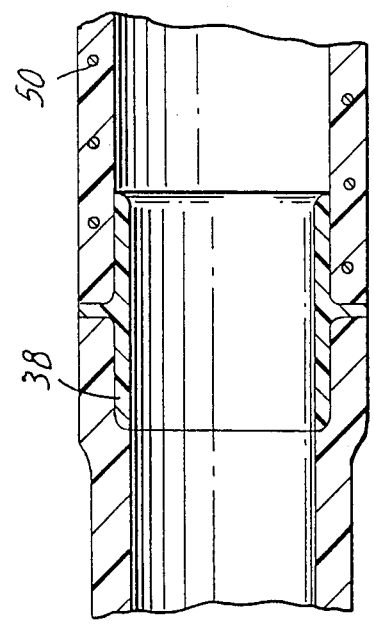
FIG. 8 is an enlarged, cross-sectional view of the medical catheter of FIG. 7, with portions broken away, taken approximately along the line 8—8 of FIG. 7.

As perhaps best shown in FIG. 1, the medical catheter 10 of the present invention is in this embodiment preferably of a one-piece construction. By contrast, the embodiment of FIGS. 7 and 8 is of a three-piece construction with two of the pieces joined at a connector 38. This connector 38 is preferably of a telescoping nature with the pieces joined by conventional means such as cement or solvent bonding or radio frequency welding. This three-piece construction facilitates manufacturing where, as in the alternate embodiment of FIGS. 7 and 8, one piece has embedded therein in conventional fashion a helical coil 50 of reinforcing wire whereas the remainder of this embodiment is not wire reinforced.

Figure 2:
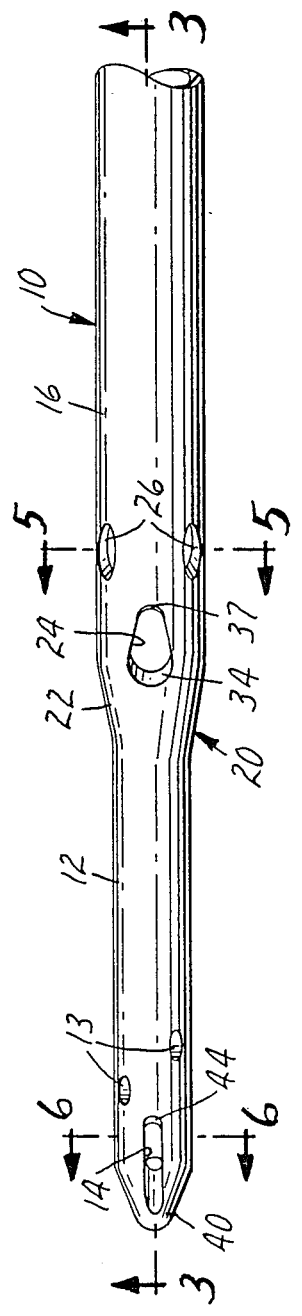
FIG. 2 is a plan view of the distal end of the medical catheter of FIG. 1.

The medical catheter 10 of FIG. 1 is preferably completely comprised, via conventional injection molding, of a medical grade polyvinyl chloride having a hardness in the range of 60 to 90 Shore A durometer about 75 Shore A durometer. This includes the distal end portion 40 having the inlet openings 14 which are preferably elongated and provides the medical catheter 10 with a relatively soft end. As perhaps best shown in FIG. 2, this soft end portion 40 is reinforced at the joining of the portions of the distal end portion 40 between the openings 14 to form the distal end, and a portion of the inlet openings 14 are preferably peripherally chamfered on the outside. Most preferably, the openings 14 are peripherally chamfered on the outside generally away from the transition catheter portion 20 with longitudinally-aligned chamfers 44. This reinforcement and chamfering reduces the likelihood of the soft end portion 40 kinking, collapsing or further damaging the already wounded heart tissue while at the same time further facilitating blood flow by further reducing the pressure drop across the medical catheter 10.

From the foregoing, it will be apparent that various modifications and changes may be made by those skilled in the art without departing from the scope and the spirit of the invention. Because these modifications and changes may be made by one skilled in the art and without departing from the scope and spirit of the invention, all matters shown and described are to be interpreted as illustrative and not in a limiting sense.

We claim:

1. A kink-resistant, dual-drainage medical catheter suitable for draining fluid from a vena cava and from a right atrium of a human heart into extracorporeal life support equipment, said catheter comprising:
   A. a first cross-sectional area catheter portion generally comprising a cylinder and dimensioned to be received within said vena cava and having at least one inlet opening;
   B. a second, larger cross-sectional area catheter portion having an outlet opening; and
   C. a transition catheter portion between said first and second catheter portions and in fluid communication with said first and second catheter portions, said transition catheter portion comprising:
      (1) means comprising a diameter-increasing protrusion adjacent said first cross-sectional area catheter portion for stinting said second, larger cross-sectional area catheter portion so that said second catheter portion cannot enter said vena cava;
      (2) a plurality of inlet openings adjacent said stinting means; said inlet openings comprising:
         (a) a plurality of generally triangularly-shaped and peripherally chamfered opening disposed about said transition catheter portion adjacent said diameter-increasing protrusion and pointing generally away from said first cross-sectional area catheter portion; and
         (b) a plurality of generally elongate and peripherally chamferred openings disposed about said transition catheter portion adjacent said triangularly-shaped openings; and
      (3) a plurality of generally longitudinally-aligned, reinforcing channels disposed along the inside of said transition catheter portion with one end of each of said channels connected to said inlet openings and the other ends of said channels connected to said second, larger cross-sectional area catheter portion, so that fluid entering said inlet openings is channeled into said second, larger cross-sectional area catheter portion together with fluid entering said inlet opening of said first cross-sectional area catheter portion.

2. A kink-resistant, dual-drainage medical catheter suitable for draining fluid from a vena cava and from a right atrium of a human heart into extracorporeal life support equipment, said catheter comprising:
   A. a first cross-sectional area catheter portion generally comprising a cylinder and dimensioned to be received within said vena cava and having at least one inlet opening;
   B. a second, larger cross-sectional area catheter portion having an outlet opening; and
   C. a transition catheter portion between said first and second catheter portions and in fluid communication with said first and second catheter portions, said transition catheter portion comprising:
      (1) means comprising a diameter-increasing protrusion adjacent said first cross-sectional area catheter portion for stinting said second, larger cross-sectional area catheter portion so that said second catheter portion cannot enter said vena cava;
      (2) a plurality of inlet openings adjacent said stinting means; said inlet openings comprising:
         (a) a plurality of generally triangularly-shaped and peripherally chamfered opening disposed about said transition catheter portion adjacent said diameter-increasing protrusion; and
         (b) a plurality of generally elongate and peripherally chamferred openings disposed about said transition catheter portion adjacent said triangularly-shaped openings; and
      wherein:
         (a) said triangularly-shaped openings are generally equidistantly disposed about said transition catheter portion with one side of each triangle generally transverse to the length of said catheter; and
         (b) said elongate openings are generally equidistantly disposed about said transition catheter portion offset from said triangularly-shaped openings, so that said channels connected to said triangularly-shaped openings have common walls with said channels connected to said elongate openings; and
      (3) a plurality of generally longitudinally-aligned, reinforcing channels disposed along the inside of said transition catheter portion with one end of each of said channels connected to said inlet openings and the other ends of said channels connected to said second, larger cross-sectional area catheter portion, so that fluid entering said inlet openings is channeled into said second, larger cross-sectional area catheter portion together with fluid entering said inlet opening of said first cross-sectional area catheter portion.

3. The medical catheter according to claim 2 wherein said catheter consists of a medical grade plastic material having a hardness in the range of 60 to 90 Shore A durometer.

4. The medical catheter according to claim 3 wherein plastic material consists of a polyvinyl chloride material having a hardness of about 75 Shore A durometer.

5. The medical catheter according to claim 3 further comprising a distal end portion having a plurality of generally elongate and peripherally chamfered openings disposed about said distal end portion and reinforced at the joining of the portions of said distal end.

6. The medical catheter according to claim 1 wherein said catheter consists of a medical grade plastic material having a hardness in the range of 60 to 90 Shore A durometer.

7. The medical catheter according to claim 6 wherein said plastic material consists of a polyvinyl chloride material having a hardness of about 75 Shore A durometer.

8. The medical catheter according to claim 6 further comprising a distal end portion having a plurality of generally elongate and peripherally chamfered openings disposed about said distal end portion and reinforced at the joining of the portions of said distal end portion between said openings to form a joined distal end.

9. A kink-resistant, dual-drainage medical catheter suitable for draining fluid from a vena cava and from a right atrium of a human heart into extracorporeal life support equipment, said catheter comprising:
   A. a first cross-sectional area catheter portion dimensioned to be received within said vena cava and having at least one inlet opening;
   B. a second, larger cross-sectional area catheter portion having an outlet opening; and
   C. a tapered transition catheter portion between said first and second catheter portions in a fluid communication with said first and second catheter portions, said transition catheter portion having a plurality of inlet openings at least a portion of which are peripherally chamfered on the inside generally away from the first cross-sectional area catheter portion.

10. The medical catheter according to claim 9 wherein said chamfering is between 30° and 70° with respect to the length of said catheter.

11. The medical catheter according to claim 10 wherein said chamfering is about 45°.

12. The medical catheter according to claim 10 further comprising a plurality of generally longitudinally-aligned, reinforcing channels disposed along with the inside of said transition catheter portion with one end of each of said channels connected to said inlet openings of said transition catheter portion and the other ends of said channels connected to said second, larger cross-sectional area catheter portion, so that fluid entering said inlet openings of said transition catheter portion is channeled into said second, larger cross-sectional area catheter portion together, with fluid entering said inlet opening of said first cross-sectional area catheter portion.

13. The medical catheter according to claim 12 wherein said inlet openings of said transition catheter portion comprise:
   A. a plurality of generally triangularly-shaped openings disposed about said transition catheter portion and pointing generally away from said first cross-sectional area catheter portion; and
   B. a plurality of generally elongate openings disposed about said transition catheter portion adjacent said triangularly-shaped openings.

14. A kink-resistant, dual-drainage medical catheter suitable for draining fluid from a vena cava and from a right atrium of a human heart into extracorporeal life support equipment, said catheter comprising:
   A. a first cross-sectional area catheter portion dimensioned to be received within said vena cava and having at least one inlet opening;
   B. a second, larger cross-sectional area catheter portion having an outlet opening; and
   C. a tapered transition catheter portion between said first and second catheter portions in a fluid communication with said first and second catheter portions, said transition catheter portion having a plurality of inlet openings at least a portion of which are peripherally chamfered on the inside generally away from the first cross-sectional area catheter portion between 30° and 70° with respect to the length of the catheter, said inlet openings comprising:
      (1) a plurality of generally triangularly-shaped openings disposed about said transition catheter portion; and
      (2) a plurality of generally elongate openings disposed about said transition catheter portion adjacent said triangularly-shaped openings; and
   wherein:
      (1) said triangularly-shaped openings are generally equidistantly disposed about said transition catheter portion with one side of each triangle generally transverse to the length of said catheter; and
      (2) said elongate openings are generally equidistantly disposed about said transition catheter portion off-set from said triangularly-shaped openings; and
   D. a plurality of generally longitudinally-aligned, reinforcing channels disposed along the inside of said transition catheter portion with one end of each of said channels connected to said inlet openings and the other ends of said channels connected to said second, larger cross-sectional area catheter portion, so that said channels connected to said triangularly-shaped openings have common walls with said channels connected to said elongate openings and so that the fluid entering said inlet openings is channeled into said second, larger cross-sectional area catheter portion together with fluid entering said inlet opening of said first cross-sectional area catheter portion.

15. The medical catheter according to claim 14 wherein at least a portion of said inlet openings of said transition catheter portion are peripherally chamfered on the outside generally towards and away from the first cross-sectional area catheter portion.

16. The medical catheter according to claim 15 wherein said catheter consists of a medical grade plastic material having a hardness in the range of 60 to 90 Shore A durometer.

17. The medical catheter according to claim 16 wherein said plastic material consists of a polyvinyl chloride material having a hardness of about 75 Shore A durometer.

18. The medical catheter according to claim 17 further comprising a distal end portion having a plurality of generally elongate openings and wherein said openings of said distal end portion are peripherally chamfered on the outside generally away from said transition catheter portion.

* * * * *

UNITED STATES PATENT AND TRADEMARK OFFICE
CERTIFICATE OF CORRECTION

PATENT NO. : 4,863,441

DATED : September 5, 1989

INVENTOR(S) : Erin J. Lindsay and James B. Howell

It is certified that error appears in the above-identified patent and that said Letters Patent is hereby corrected as shown below:

Col. 4/Line 57, "durometer about 75" should read --durometer and preferably about 75--.

Col. 5/Line 39, "opening" should read --openings--.

Col. 5/Line 45, "chamferred" should read --chamfered--.

Col. 6/Line 14, "opening" should read --openings--.

Col. 6/Line 18, "chamferred" should read --chamfered--.

Col. 6/Line 50, "wherein plastic" should read --wherein said plastic--.

Col. 6/Line 56, "distal end." should read --distal end portion between said openings to form a joined distal end.--

Col. 7/Line 37, "together," should read --together--.

Signed and Sealed this

Fourth Day of September, 1990

Attest:

HARRY F. MANBECK, JR.

*Attesting Officer*      *Commissioner of Patents and Trademarks*